(12) United States Patent
Rosen et al.

(10) Patent No.: US 11,931,473 B2
(45) Date of Patent: Mar. 19, 2024

(54) HANDHELD ULTRAVIOLET IRRADIATION DEVICE HAVING DISTANCE MEASUREMENT SYSTEM

(71) Applicant: FREESTYLE PARTNERS, LLC, Detroit, MI (US)

(72) Inventors: Jennifer K Rosen, Detroit, MI (US); Gregory D. DeGrazia, Birmingham, MI (US); Benjamin X. Feeney, Nashville, TN (US); Josiah LaColla, Farmington Hills, MI (US); Kevin Martin, Brentwood, TN (US); Prasanna Natarajan, Wixom, MI (US); Joseph M. Schmondiuk, III, Rochester, MI (US); David Thimm, Plymouth, MI (US)

(73) Assignee: FREESTYLE PARTNERS LLC, Detroit, MI (US)

( * ) Notice: Subject to any disclaimer, the term of this patent is extended or adjusted under 35 U.S.C. 154(b) by 223 days.

(21) Appl. No.: 17/333,558

(22) Filed: May 28, 2021

(65) Prior Publication Data

US 2021/0283289 A1  Sep. 16, 2021

Related U.S. Application Data

(63) Continuation of application No. 17/119,440, filed on Dec. 11, 2020, now Pat. No. 11,020,501, which is a
(Continued)

(51) Int. Cl.
*A61L 2/10* (2006.01)
*A61L 2/26* (2006.01)

(52) U.S. Cl.
CPC ............... *A61L 2/10* (2013.01); *A61L 2/26* (2013.01); *A61L 2202/11* (2013.01); *A61L 2202/14* (2013.01)

(58) Field of Classification Search
CPC .......... A61L 2/22; A61L 2/24; A61L 2202/11; A61L 2202/14; A61L 2101/02;
(Continued)

(56) References Cited

U.S. PATENT DOCUMENTS 2,215,635 A   9/1940   Collins
2,720,145 A   10/1955  Goodfellow
(Continued)

FOREIGN PATENT DOCUMENTS

CN   2598810 Y   1/2004
CN   2619817     6/2004
(Continued)

OTHER PUBLICATIONS

PCT/US2021/043946 International Search Report and Written Opinion dated Nov. 18, 2021.
(Continued)

*Primary Examiner* — Timothy C Cleveland
(74) *Attorney, Agent, or Firm* — Gregory D. DeGrazia; Miller, Canfield, Paddock and Stone

(57) ABSTRACT

A handheld light assembly for eradicating pathogens includes a housing. A processor and a lamp are disposed inside the housing. The lamp irradiates surfaces with disinfecting ultraviolet light having a peak wavelength of 222 nm filtered to restrict illumination to between 200 nm and 230 nm within an irradiation zone. A distance measuring system includes a secondary light source generating secondary light and a photodetector for measuring distance of the secondary light to a surface being irradiated by the lamp light being reflected from the surface to the photodetector. The secondary light source is offset at an angle from the lamp thereby projecting the light beam to a central area of the irradiation zone generated by the lamp. The photodetector signals the processor to calculate a vertical distance between the lamp
(Continued)

and the central area of the irradiation zone on the surface being irradiated from an angular projection of the secondary light.

16 Claims, 4 Drawing Sheets

Related U.S. Application Data continuation-in-part of application No. 16/809,976, filed on Mar. 5, 2020, now Pat. No. 11,071,799, said application No. 17/119,440 is a continuation-in-part of application No. 16/279,253, filed on Feb. 19, 2019.

(60) Provisional application No. 62/963,682, filed on Jan. 21, 2020, provisional application No. 62/694,482, filed on Jul. 6, 2018, provisional application No. 62/632,716, filed on Feb. 20, 2018.

(58) Field of Classification Search
CPC .............. B01J 19/088; B01J 2219/0801; B01J 2219/0805; B01J 2219/0869; B01J 2219/0896
See application file for complete search history.

(56) References Cited

U.S. PATENT DOCUMENTS

| | | |
|---|---|---|
| 5,688,475 A | 11/1997 | Duthie |
| 6,201,933 B1 | 3/2001 | Hylen |
| 6,650,085 B2 | 11/2003 | Lau et al. |
| 7,805,220 B2 | 9/2010 | Taylor |
| 8,105,532 B2 | 1/2012 | Harmon et al. |
| 8,142,715 B2 | 3/2012 | Curry et al. |
| 8,357,914 B1 | 1/2013 | Caldwell |
| 8,753,575 B2 | 6/2014 | Neister |
| 8,847,174 B2 | 9/2014 | Domenig |
| 9,572,903 B2 | 2/2017 | Dobrinsky et al. |
| 9,649,398 B1 | 5/2017 | York |
| 9,700,642 B2 | 7/2017 | Neister |
| 9,767,337 B2 | 9/2017 | Furlong |
| 10,228,622 B2 | 3/2019 | Kimsey-Lin |
| 2003/0113230 A1 | 6/2003 | Cordery et al. |
| 2003/0179456 A1 | 9/2003 | Uchida et al. |
| 2006/0188389 A1 | 8/2006 | Levy |
| 2007/0053188 A1 | 3/2007 | New et al. |
| 2007/0075063 A1 | 4/2007 | Wilbanks et al. |
| 2007/0097351 A1 | 5/2007 | York et al. |
| 2008/0103560 A1 | 5/2008 | Powell |
| 2008/0295271 A1 | 12/2008 | Perunicic |
| 2008/0310996 A1 | 12/2008 | Kim et al. |
| 2010/0104471 A1 | 4/2010 | Harmon |
| 2010/0118528 A1 | 5/2010 | Ryan |
| 2011/0256019 A1 | 10/2011 | Gruen et al. |
| 2014/0063261 A1 | 3/2014 | Betensky et al. |
| 2015/0190537 A1 | 7/2015 | Kerr |
| 2016/0101202 A1 | 4/2016 | Gil et al. |
| 2017/0069192 A1 | 3/2017 | Sood et al. |
| 2017/0080251 A1 | 3/2017 | Yehezkel |
| 2017/0157276 A1 | 6/2017 | Dobrinksy |
| 2017/0182305 A1 | 6/2017 | Kermode et al. |
| 2017/0216466 A1 | 8/2017 | Dujowich et al. |
| 2017/0216472 A1 | 8/2017 | Stibich et al. |
| 2017/0225206 A1 | 8/2017 | Deitchman |
| 2017/0245616 A1 | 8/2017 | Lakios et al. |
| 2018/0117194 A1 | 5/2018 | Dobrinksy et al. |
| 2018/0118337 A1 | 5/2018 | Viel |
| 2018/0236113 A1 | 8/2018 | Gross |
| 2019/0255201 A1 | 8/2019 | Rosen et al. |
| 2019/0388572 A1 | 12/2019 | Cole et al. |
| 2020/0078483 A1 | 3/2020 | Eldman |
| 2020/0215214 A1 | 7/2020 | Rosen et al. |
| 2021/0355581 A1 | 11/2021 | Zhao et al. |
| 2021/0393819 A1 | 12/2021 | Kim et al. |

FOREIGN PATENT DOCUMENTS

| | | |
|---|---|---|
| CN | 1548311 A | 11/2004 |
| CN | 101839581 A | 9/2010 |
| CN | 202896237 U | 4/2013 |
| CN | 107613895 A | 1/2018 |
| CN | 107997851 A | 5/2018 |
| CN | 208974695 U | 6/2019 |
| GB | 2433201 A | 6/2007 |
| GB | 2500168 A | 9/2013 |
| JP | 2012/254673 A | 12/2012 |
| JP | 2019-042487 A | 3/2019 |
| JP | 2019536492 A | 12/2019 |
| KR | 0178167 B1 | 8/1998 |
| WO | 2022023007 A1 | 2/2002 |
| WO | 2008145906 A | 12/2008 |
| WO | 2016196904 A1 | 12/2016 |
| WO | 2018164845 A1 | 9/2018 |
| WO | 2019/132991 A | 7/2019 |
| WO | 2019164810 A1 | 8/2019 |
| WO | 2019241453 A1 | 12/2019 |

OTHER PUBLICATIONS

Buonanno et al. Germicidal Efficacy and Mammalian Skin Safety of 222-nm UV Light; Radiation Research 187, 493-501 (2017) (Year 2017).

Coxworth, "Human-safe ultraviolet light used to kill airborne viruses" New Atlas article, Feb. 9, 2018, https://newatlas.com/far-uvc-airborne-viruses/53349/.

Lapook, "How Ultraviolet light could be used to fight the flu" CBS news, Feb. 12, 2018, https://www.cbsnews.com/new/how-ultraviolet-light-could-be-used-to-fight-the-flu/.

Narita, Chronic Irradiation with 222-nm UVC light induces neither DNA damage nor epidermal lesions in mouse skin, Jul. 25, 2018.

Nerandzic et al., "Evaluation of a hand-held far-ultraviolet radiation device for decontamination of Clostridium difficile and other healthcare-associated pathogens" U.S. National Library of Medicine, National Institutes of Health, BMC Infect. Dis. May 16, 20212.

Welch et al. "Far-UVA light: A new tool to control the spread of airborne-mediated microbial diseases" Scientific Reports 8, Article No. 2752, Feb. 9, 2018, https://www.nature.com/articles/s41598-018-21058-w.

PCT/US2019/018517 International Search Report and Written Opinion dated Jun. 20, 2019.

PCT/US2020/066056 International Search Report and Written Opinion dated Mar. 23, 2021.

PCT/US2021/014386 International Search Report and Written Opinion dated Apr. 9, 2021.

Extended European Search Report issued by the European Patent Office in European Patent Application 21191961.8, dated Dec. 23, 2021.

Notification of Transmittal of The International Search Report for PCT/US23/14269 dated May 15, 2023.

Notification of Reasons for Rejection-From the Japanese Patent Office, dated Feb. 28, 2023 issued in corresponding Japanese patent application: 2022-544280.

Notification of Reasons for Rejection for JP Appln 2022-559866 dated Jun. 27, 23 (Machine Translation).

Illinois Tool Works—CN107997851 (A) dated: May 8, 2018 (Machine Translation).

Li Jinyuan—CN2619817 (Y) dated: Jun. 9, 2004 (Machine Translation).

Zhejiang Geely—CN202896237 (U) dated: Apr. 24, 2013 (Machine Translation).

First Office Action for Chinese Application No. 2021800337193.3 dated May 23, 2023 (Machine Translation).

Shi Guojian—CN1548311 (A) dated: Nov. 24, 2004 (Machine Translation).

Han Xiangkun—CN2598810 (Y) dated: Jan. 14, 2004 (Machine Translation).

Zhejiang Dunan—CN101839581 (A) dated: Sep. 22, 2010 (Machine Translation).

(56) References Cited

OTHER PUBLICATIONS

Univ. Columbia—CN107613895 (A) dated: Jan. 19, 2018 (Machine Translation).

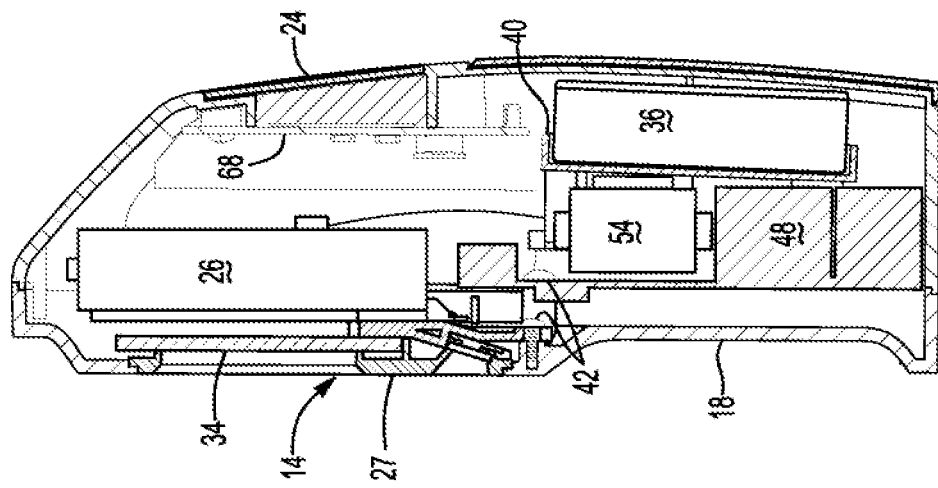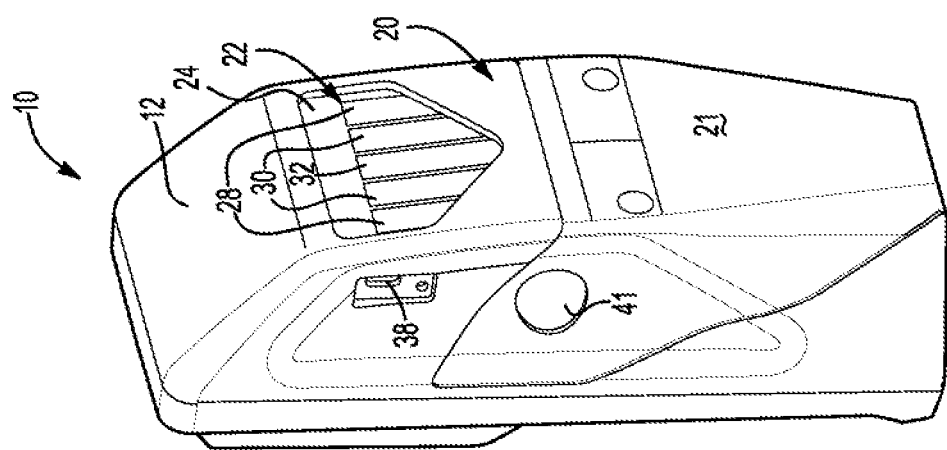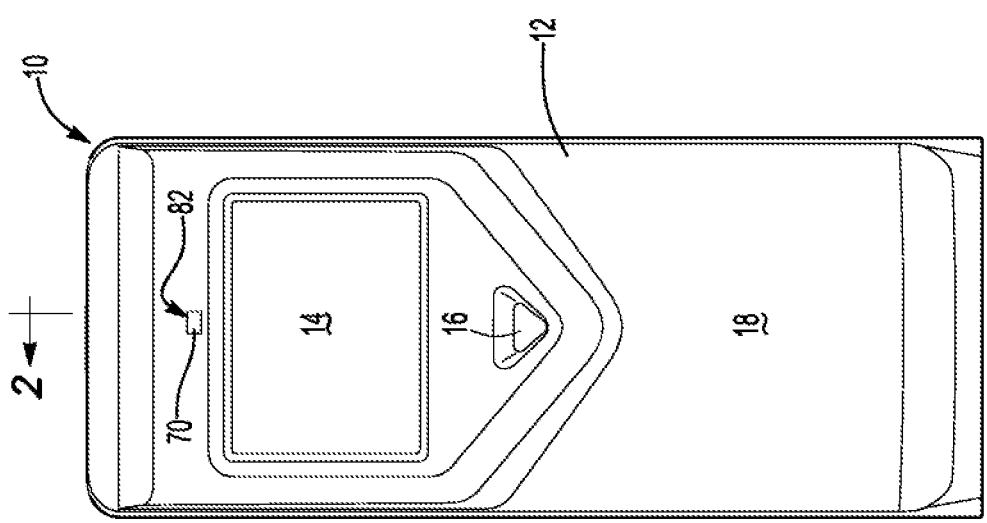

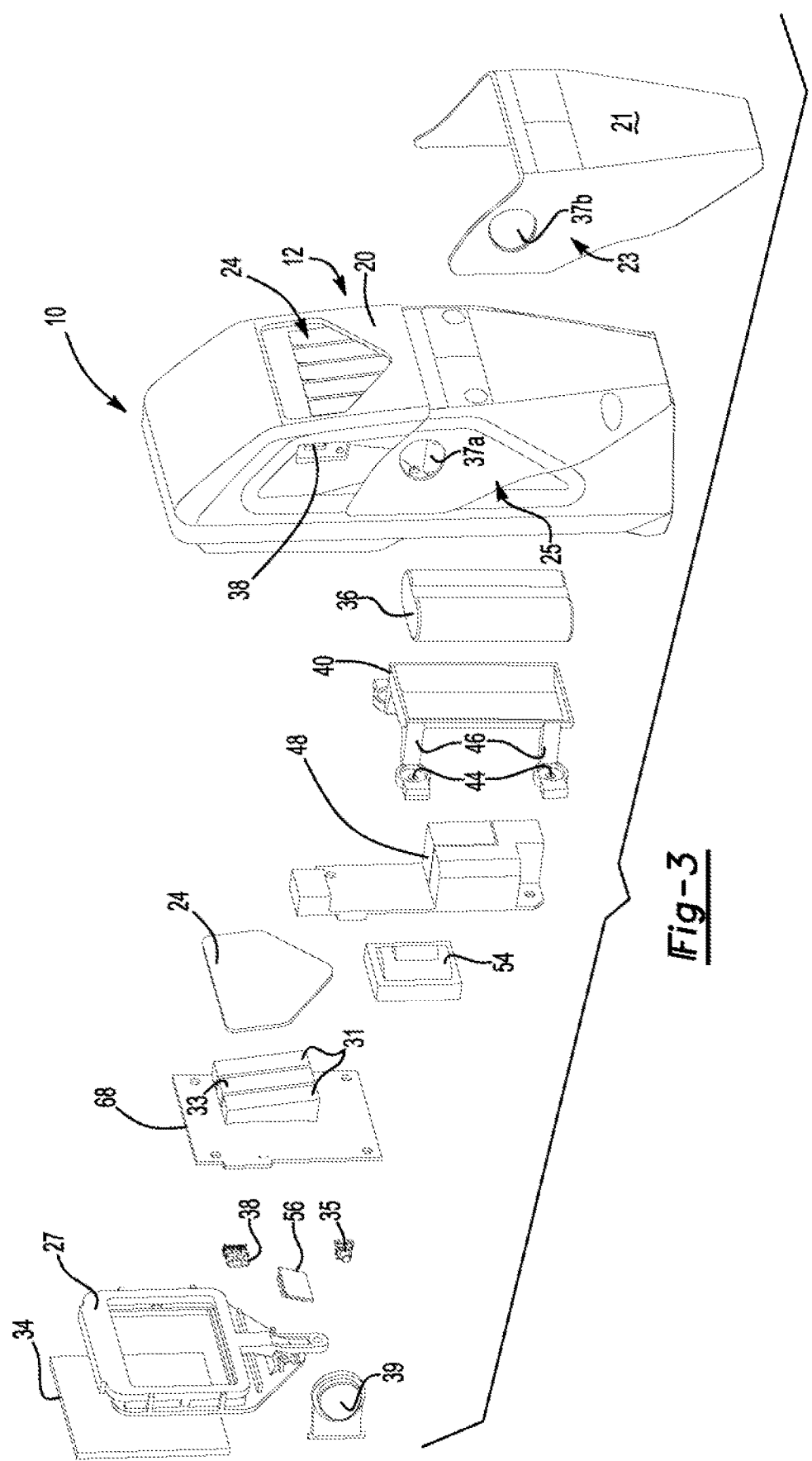

HANDHELD ULTRAVIOLET IRRADIATION DEVICE HAVING DISTANCE MEASUREMENT SYSTEM

PRIOR APPLICATIONS

The present application claims priority as a Continuation-In-Part to U.S. patent application Ser. No. 16/809,976 filed Mar. 5, 2020 that claims priority to Provisional Patent Application No. 62/963,682, filed Jan. 21, 2020, each of which is hereby incorporated herein by reference in its entirety. The present application also claims priority as a Continuation-In-Part to U.S. patent application Ser. No. 16/279,253, filed Feb. 19, 2019 that claims priority to Provisional Patent Application No. 62/694,482, filed Jul. 6, 2018, and to Provisional Patent Application No. 62/632,716, filed Feb. 20, 2018, which are all incorporated herein by reference in their entireties.

TECHNICAL FIELD

The present application relates generally toward a handheld device used for eradicating pathogens on a surface and surrounding area. More specifically, the present application is directed toward a handheld, far-ultraviolet handheld device that rapidly eradicates pathogens on at least surfaces while also being safe for human exposure.

BACKGROUND

With the rapid expansion of biological pathogens, it has become increasingly important to find novel ways to eradicate pathogens in a manner that is safe for human exposure. Increasingly, chemicals have been implemented to disinfect surface is in public places. However, the increased use in chemicals is presenting health hazards that are only beginning to be manifest. In response to an increased need in an eradication of biological pathogens, various forms of ultraviolet light have been developed to disinfect aerosol pathogens and surface pathogens.

The use of ultraviolet light has proven particularly effective for eradicating pathogens when ultraviolet-C (UVC) light is incorporated into an illumination device. UVC light emissions range between about 100 nm and 280 nm. While UVC light has proven quite effective in eradicating pathogens, it is known to exhibit unsafe attributes when exposed to human epidermis and eye tissue. Conventional UVC light has been proven to cause skin cancer and cataracts. Therefore, the use of UVC light is limited in scope to situations where no human exposure is permitted and substantial precautions are required to prevent any human exposure. A subset of UVC light has gained some notoriety of late come up which is commonly referred to as far-UVC light.

While far-UVC light has shown promise for eradication of pathogens, its proposed uses have been for ceiling mounted systems for eradicating aerosol pathogens providing slow eradication on distant surfaces taking upwards of thirty minutes. Therefore, there exists a need for a device capable of rapidly eradicating pathogens, particularly on surfaces and epidermis that does not cause adverse health issues.

SUMMARY

A handheld assembly for eradicating pathogens is disclosed. The assembly includes a housing and a processor. A lamp is disposed in the housing for irradiating surfaces with disinfecting ultraviolet light, in one embodiment, having a peak wavelength of about 222 nm and being filtered to restrict illumination to between about 200 nm and 230 nm. In another embodiment, the ultraviolet light is not filtered providing illumination up to about 240 nm. The lamp generates an irradiation zone upon a surface being irradiated.

A distance measuring system includes, in one embodiment, a secondary light source generating a beam of light and a photodetector for measuring distance of the lamp to the surface being irradiated by the lamp from the beam of light being reflected from the surface to the photodetector. The secondary light source is offset at an angle from the lamp thereby projecting the light beam to a central area of the irradiation zone generated by the lamp. The photodetector signals the processor to calculate a distance between the lamp and the central area of the irradiation zone on the surface being irradiated.

The assembly of the present invention is capable of rapidly eradicating pathogens on surfaces when located a predetermined, and precise distance from the surface being irradiated. The lamp is capable of, when held at the proper distance, eradicating pathogens such as, for example, COVID-19, influenza another viruses, bacteria, mold and infectious spores. The difference between, for example one inch and six inches from a surface can result in a tenfold increase in the amount of time required to eradicate pathogens. When the handheld device of the present application is held at the proper distance, COVID-19 is eradicated by as much as 99.9% in less than about one second. Most bacteria can be eradicated in less than about three seconds. Long distance eradication with, for example, a UVC lamp mounted on a ceiling requires as much as thirty minutes to achieve a 99.9% reduction for pathogens. Because ceiling mounted UVC illumination devices require tens of minutes to eradicate pathogens on surfaces and are not practical in highly used places requiring rapid eradication, such as, for example, doctor's offices, restaurants, banks, hotel lobbies, airplanes, etc.

A further benefit of the assembly of the present invention is that the epidermis may also be safely disinfected through illumination expanding the uses of the assembly. For example, eating utensils at a table in restaurant, groceries, even food delivered to table can be irradiated for eradicating pathogens in only a few seconds while still being safe for human exposure. Protective equipment such as glove and goggles as are commonly required with ultraviolet devices are not necessary as are required of UVC lamps that irradiated above 230 nm.

BRIEF DESCRIPTION OF THE DRAWINGS

Other advantages of the present invention will be readily appreciated as the same becomes better understood by reference to the following detailed description, when considered in connection with the accompanying drawing, wherein:

FIG. 1A shows a face side view of the handheld device of the present invention;

FIG. 1B shows a backside perspective view of the handheld device of the present invention;

FIG. 2 shows a cross-sectional view along a centerline of the view shown in FIG. 1;

FIG. 3 shows an exploded view of the handheld device of the present invention;

DETAILED DESCRIPTION

Figure 4:
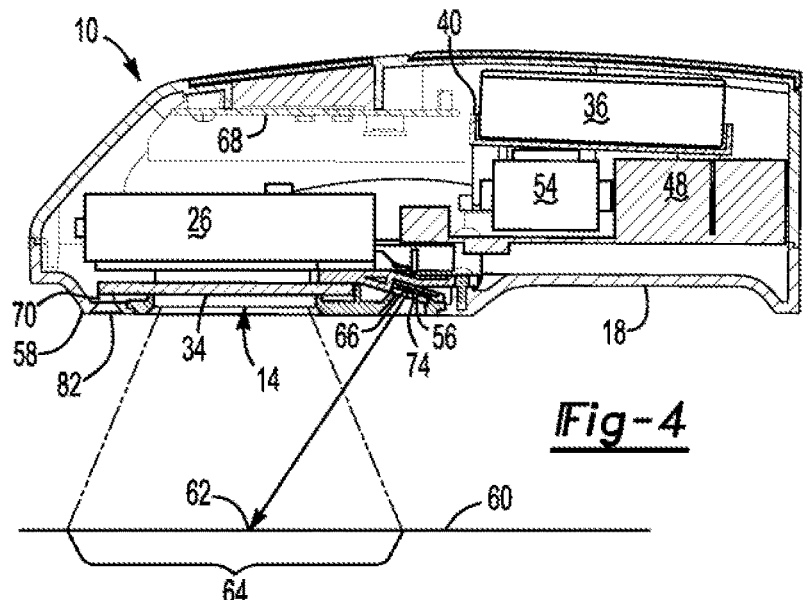
FIG. 4 shows a cross-sectional view of the handheld device of the present invention having the distance measuring device activated.

Referring to FIG. 1A, a handheld light assembly of the present invention is generally shown at 10. The assembly 10 includes a housing 12 that defines a lamp opening 14 as will be explained further herein below. A secondary light opening 16 is defined by the housing 12 approximate the lamp opening 14. Both openings 14,16 are defined by a face side 18 of the housing 12. The purpose of the lamp opening 14 in the secondary light opening 16 will be explained further herein below.

The housing 12, as best shown in FIG. 1B includes a backside 20 that defines an indicator opening 22. A removable grip 21 receives the backside 20 of the housing 12 and is removably retained by the complementary abutting surfaces 23, 25 (FIG. 3) respectively that each defines a convex shape providing an interference retention system. The removable grip 21 is cleanable by way of illumination with the assembly 10 as will become more evident herein below or is cleanable by alternative methods in a desired manner. When mated, the face side 18 and the backside 20 define a stand 19 so that the assembly 10 may stand upright, when desired, orienting the lamp 14 in a vertical direction.

An indicator 24 encloses the indicator opening 22. The indicator 24 signals an operator weather a distance between a lamp 26 (FIG. 4) and a surface being irradiated his within a predetermined distance to a pathogen to provide optimal eradication energy. For example, a first telltale 28 signals the operator if the distance is beyond a predetermined distance (or in some instances not spaced enough). In one embodiment, the telltale illuminates red or other color signaling the operator if the lamp is too far, or too close. The indicator 24 generate a second signal by way of 2 nd telltale 30 indicating when the lamp is proximate the predetermined distance to the surface being irradiated. In one embodiment, the second telltale illuminates in yellow to signal the lamp 26 is proximate the predetermined distance to the surface 60 (FIG. 4) being irradiated. When the lamp 26 is at the predetermined distance to the surface being irradiated, a third telltale 32 illuminates in green to signal the operator the lamp is operating at optimal efficiency at the predetermined distance. Each telltale 28, 30, 32 is illuminated by a corresponding light 29, 31, 33 (FIG. 3) respectively, in this embodiment a corresponding light emitting diode.

It should be understood to those of ordinary skill in the art the different telltales or indicators may be used to signal an operator whether the assembly 10 is being used properly by way of distance from a surface being disinfected. These include, but are not limited to, blinking lights, sound feedback, or any indicator that would suffice to signal an operator the lamp 26 is disposed at the proper distance from a surface being irradiated for providing optimal eradication of pathogens.

While "surface" is used throughout the application, it should be understood that the invention of the present application provides for rapid eradication of pathogens not only on inanimate object, but also on epidermis including hands, legs arms, and even a face of an individual. As will be explained further herein below, disinfecting skin at a rapid pace is now possible without requiring the use of soap or chemicals. In a matter of seconds an individuals hands my disinfected with the handheld assembly 10 of the present invention. Furthermore, abrasions and wounds may also be rapidly disinfected in a safe and immediate manner while awaiting administered antibiotics to begin working.

Referring now to FIG. 3, the lamp 26 is activated by depressing switch 35 that partially extends through opening 37a defined by the backside 20 of the housing 12 and an opening 37b defined the removable grip 21, each of which are aligned the removable grip 21 is disposed in place on the housing 12. A switch cover 39 is disposed between the switch 35 and the backside 20 of the housing and conceals the switch 35 so that when depressed, an operator does not contact the switch 35 but contacts the switch cover 39. A still further embodiment includes a protective barrier 41 being affixed, either permanently or temporarily to the removal grip 21 over the grip opening 37b to prevent the switch cover 39 from becoming contaminated. In this manner the barrier 41 may also be disinfected with the grip 21 when removed from the housing 12. In one embodiment, when the assembly 10 is supported in vertical direction by the stand 19, the switch 35 optionally activates the processor 68 to power the lamp 26 for a predetermined amount of time allowing a user to disinfect, for example his or her hands, the removable grip 21, or any other object without continuously depressing the switch 35, or even having to hold the device. Because the illumination wavelength of the lamp 26 is filtered restricting transmission wavelength to below 230 nm, and not harmful to eyes and epidermis, the lamp may be illumined while disposed in a vertical orientation while riot requiring the use of safety equipment.

Referring now to FIG. 2, a cross sectional view through line 2-2 of FIG. 1A is shown. The lamp 26 is disposed over the lamp opening 14 in a fixed location by lamp frame 27 for generating illumination through the lamp opening 14 onto a target surface 60. The lamp 26 is adapted to use a variety of illumination devices including krypton chloride tubes, light emitting diodes, or any other illumination system capable of transmitting light at a peak wavelength 222 nm. In one embodiment, the lamp 26 is filtered to eliminate light having a wavelength above about 230 nm. Therefore, disinfecting light is transmitted at a wavelength between about 200 nm and 230 nm. In one embodiment, fused silica glass 34, or equivalent is placed over the lamp opening 14 to protect the lamp during use. Fused silica glass 34 is believed durable enough to withstand the energy generated by UVC light emissions without significant degradation while allowing light transmission without significantly reducing irradiation power of the lamp 26.

The lamp 26 is powered via power pack 36. The power pack 36 is rechargeable through plug-in charging port 38. In one embodiment, the power pack 36 includes two lithium ion 18650 PMI cells (not shown) providing about 3.6 volts each. Therefore, the power pack 36, when charged, provides about 7.2 volts. Alternatively, the lamp 26 is powered by electrical current provided through the charging port 36. The power pack 38 is received by a power pack support 40 that secures the power pack 36 to screw bosses located on an inner surface of the face side 18 of the housing 12 via fasteners (not shown) in a known manner. The fasteners are received through support apertures 44 defined by support legs 46.

The support legs 46 allow the power pack support 40 to straddle an inverter 48 that is also secured to the face side 18 of the housing 12. The inverter 48 receives current from the power pack 36 at 7.2 volts and shapes the current wavelength in a known manner so it that may be received by the lamp 26. The inverter 48 is disposed upon an inverter frame 50 that is secured to the face side 18 of the housing 12 by fasteners received through inverter frame apertures 52.

A transformer 54 steps up the voltage from about 7.2 volts generated by the power pack 36 to about 4,000 volts to provide sufficient energy to power the lamp 26. In one embodiment, the inverter 48 is a Stratheo inverter. However, it should be understood that any inverter/transformer combination capable of shaping the current wavelength and stepping up voltage to about 4,000 volts will suffice. The transformer 54 is also mounted on the inverter frame 50 to reduce overall size of the inverter 48 transformer 54 combination.

A distance measuring device 56 is secured to a lamp frame 58 that also secures the lamp 26 to the face side 18 of the of the housing 12. The lamp frame 58 is oriented so that the lamp 26 is disposed horizontally to a surface 60 being disinfected when the assembly 10 is in use as is best shown in FIG. 4. The distance measuring device 56 is offset from the lamp 26 and disposed at an angle relative to the lamp 26. In one embodiment, the distance measuring device 56 transmits a signal to center portion 62 of an irradiation zone 64 on the surface 60 defined by the lamp 26. The distance measuring device 56 includes a sensor 66 that receives reflected feedback of the signal from the center portion 62. The sensor 66 signals a process the feedback data for the processor 68 to calculate a vertical distance from the lamp 26 to the center portion 62 of the irradiation zone 64. Therefore, even though the distance measuring device 56 is offset from the lamp 26, a precise vertical distance between the lamp 26 and the surface 60 being irradiated at the location of the highest energy level, the purpose of which will become more evident as explained below.

In one embodiment, the distance measuring device 56 is a lidar system transmitting a laser beam 63 to the center portion 62 of the irradiation zone 64. The laser beam 63 is either visible or invisible. When visible, the laser beam provides user feedback to the center portion 62 of the irradiation zone 64. In another embodiment, the distance measuring device 56 takes of the form of an infrared light that transmits to the center portion 62 of the irradiation zone 64 and the sensor 66 is an infrared sensor that detects reflected light from the center portion 62 for signaling the processor to calculate vertical distance from the center portion 62 to the lamp 14. Other types of distance measuring devices are within the scope of this invention including radar, photogrammetry and the like so long as the center portion 62 of the irradiation zone 64 can be detected. It should also be understood that a time of flight determination between the light (or other signal) and sensor 66 detecting reflection has provided sufficient accuracy for the processor 68 to calculate vertical distance between the central portion 62, or point as the case may be, and the lamp 26.

As set forth above, the processor 68 signals the indicator 24 to signal if the lamp 26 is located at a predetermined distance from the center portion 62 of the irradiation zone. In one embodiment, the indicator 24 signals proper distance is maintained for rapid eradication of pathogens when the lamp 26 is disposed within a range of distances, such as, for example between one and two inches. Therefore, the user is provided feedback that the lamp 26 is maintained within in a proper range even when three dimensional surfaces are being irradiated for eradicating pathogens. It has been determined that distance is inversely proportional to the rate of energy that reaches the surface 60. The less the distance the lamp 14 is to the surface 60 being irradiated, the higher the rate of ultraviolet energy transfer to the surface 60 is achieved for rapid eradication of surface pathogens.

The lamp 14 was tested at a range of distances to ascertain the amount of energy required to eradicate pathogens, both with the fused silica 36 protective lens and without the fused silica protective lens 36. The results showed only a small decrease in the amount of far-UVC light energy when the fused silica 36 lens was employed. The results were measured in μWatts as is shown in Table 1.

TABLE 1

| Distance from Sensor | No Protective Cover | UV Fused Silica |
|---|---|---|
| 1" (2.5 cm) | 3202 | 3030 |
| 2" (5.08 cm) | 1770 | 1650 |
| 4" (10.16 cm) | 685 | 634 |
| 6" (15.24 cm) | 353 | 330 |

At a distance of about one inch from the surface 60 being irradiated, the lamp 14 provides 3030 μW rate of energy transfer. Alternatively, a distance of about six inches from the surface 60 being irradiated, the lamp 14 provides 330 μW of ultraviolet energy transfer. The amount of energy transfer translates into the amount of time necessary to eradicate certain pathogens. Test results show that Covid-19 is eradicated by providing a 3 Log reduction (99.9% eradication) in the pathogen when the lamp is spaced about one inch from the surface 60 being irradiated in about one second when the lamp 14 is disposed at a distance of about one inch from the surface 60 being irradiated. Alternatively, Covid-19 can be eradication to a 3 Log reduction in about 9.5 seconds when the lamp 14 is disposed at a distance of about six inches from the surface 60 being irradiated. It should be understood by those of ordinary skill in the art that different pathogens require different doses of irradiation for full or 3 Log reduction on any surface. While a virus may require only one second of irradiation when the lamp 14 is disposed at one inch from the surface 60 being irradiated, a bacteria or spore may require several seconds of irradiation at the same distance. Furthermore, a 2 Log reduction providing 99% eradication of Covid-19 is achieved when the lamp 26 is spaced about one inch from the surface 60 being irradiated is achieved in about 0.1 seconds. Likewise, Covid-19 can be eradication to a 2 Log reduction in about 0.95 seconds when the lamp 14 is disposed at a distance of about six inches from the surface 60 being irradiated. It should be apparent that determining an accurate distance of the lamp 26 from the surface 60 being irradiated is requisite when determining the level of a pathogen eradication being achieved.

Figure 5:
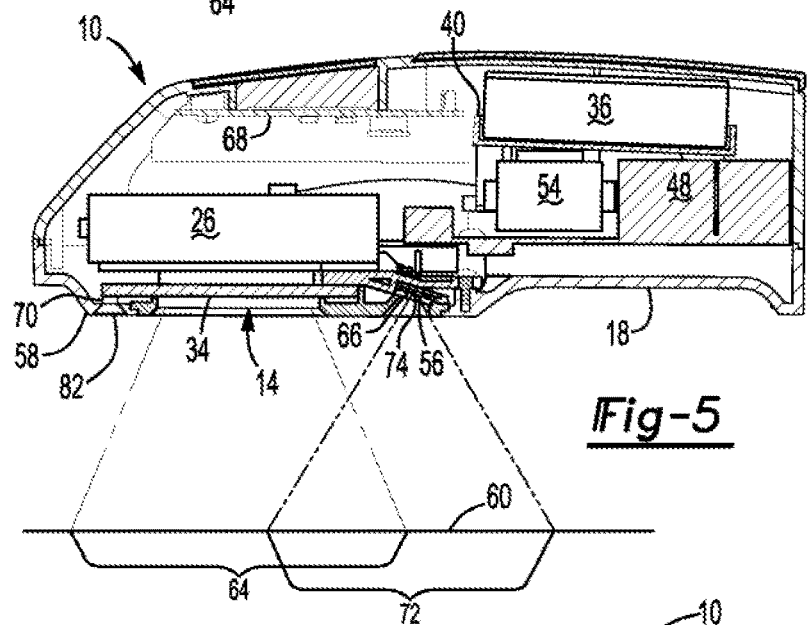
FIG. 5 shows a cross-sectional view of the handheld device of the present invention having an alternative distance measuring device activated.

FIG. 5 shows an alternative arrangement where the distance measuring device 56 includes transmits secondary light onto a measurement area 72 that intersects the irradiation zone 64 on the surface 64. In this embodiment, at least a portion of the measurement area 72 intersects the center portion 62 of the irradiation zone 64. The sensor 66 detects the reflected light, radar or the like from the irradiation zone 64 for signaling the processor 68 to calculate a vertical distance between the lamp 26 and at least the center portion 62 of the irradiation zone 64.

It should also be understood that the distance measuring device 56 includes a transmitter 74 that transmits a signal to the surface 60 being irradiated by the lamp 26. The transmitter 74 is contemplated to project any of a non-visible laser beam, a visible laser beam, infrared light, radar, or the like enabling the sensor 66 to detect a reflected signal from the surface 60 being irradiate so that the processor 68 can calculate vertical distance between the lamp 26 and at least the center portion 62 of the irradiation zone 64.

Figure 6:
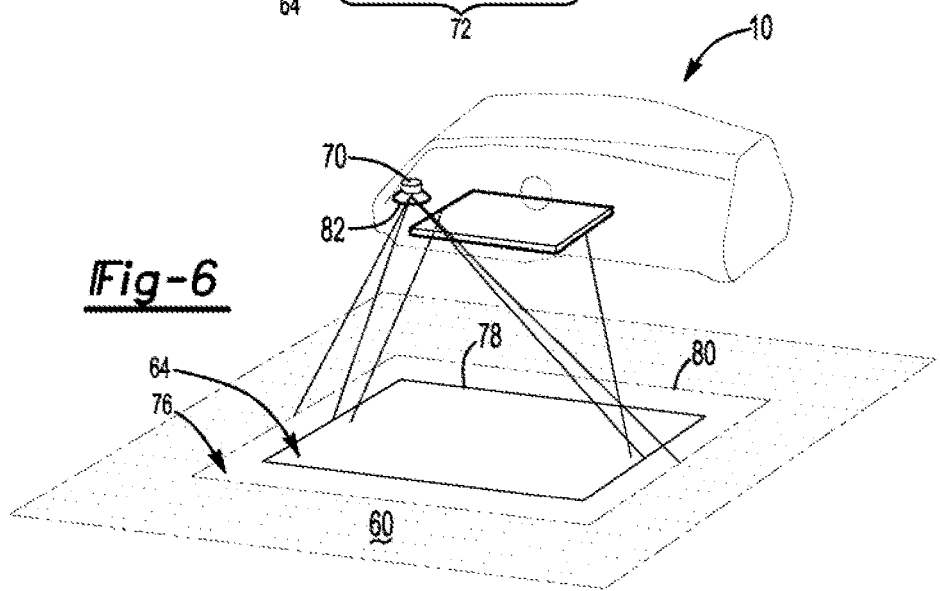
FIG. 6 shows partial perspective view of the handeld device showing a identifier light source active for identifying irradiation zones.
Figure 7:
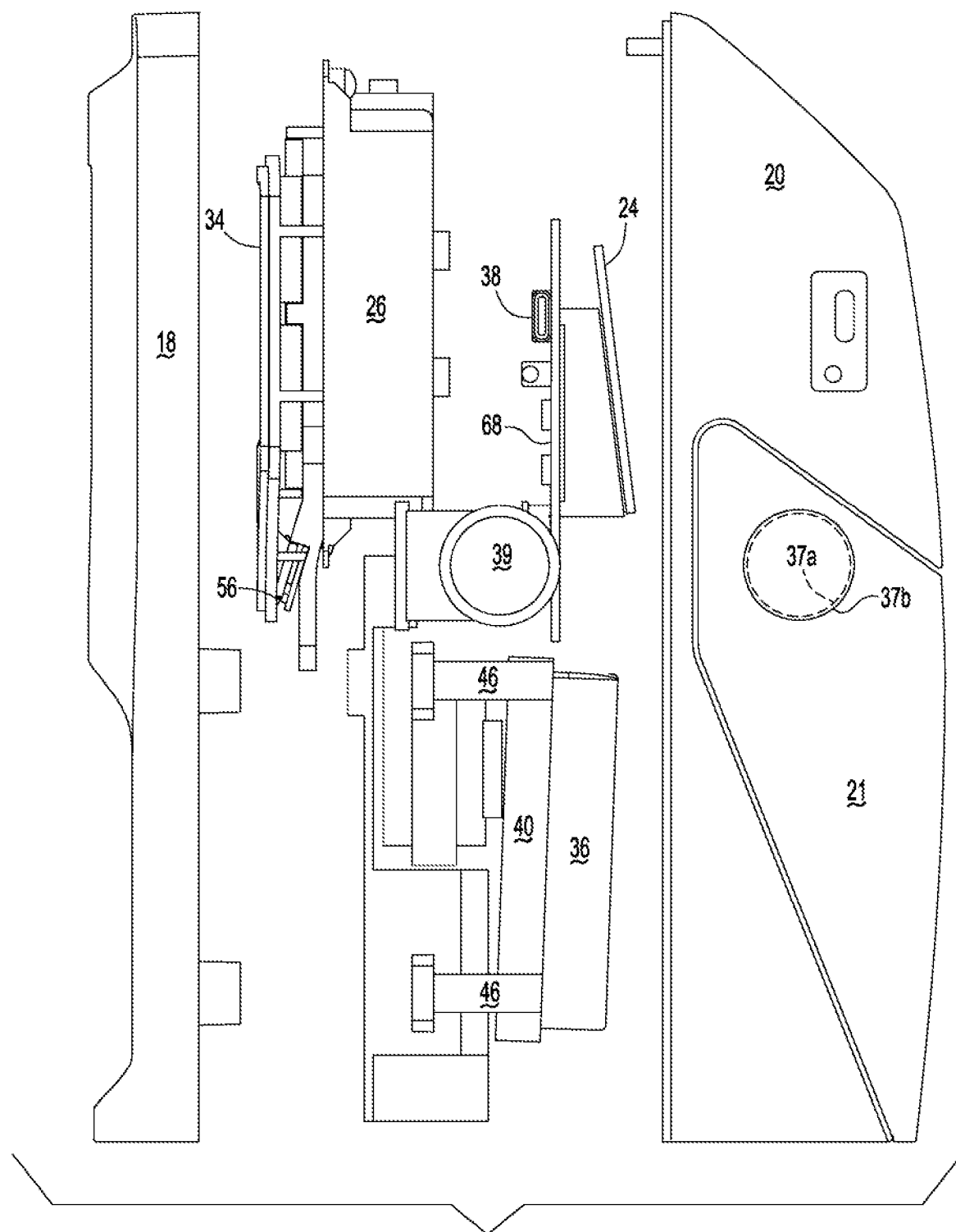
FIG. 7 shows an expanded view of the handheld device of the present invention with the housing separated.

Transmitted UVC light is largely in an invisible spectrum. Therefore, it is difficult for a user to fully identify a surface area in which the lamp 14 is achieving optimal irradiation. In addition, the lamp provides efficacy as the UVC light illumination on a surface extends radially outwardly from the central portion 62 (or area) of the irradiation zone 64. However, the energy transfer to the surface 60 diminishes beyond the irradiation zone 64 on the surface 60. While still providing efficacy, a secondary irradiation zone 76 located generally radially outwardly of the first irradiation zone 64 requires additional time in which to eradication pathogens. To assist the operator with identifying at least the irradiation zone 64, and also, when desired, a secondary irradiation zone 76, a identifier light source 70 projects a first ring 78 or equivalent around the primary irradiation zone 64 and second ring 80 or equivalent around the secondary irradiation zone 76 as is represented in FIG. 6. The identifier light source 70 is a separate light from the secondary light that is part of the distance measurement device 56.

The illumination by the identifier light source 70, in one embodiment, is modified by identifier light source lens 82 that focuses the light from the identifier light source 70 to focus the light so that the first ring 78 is disposed on the surface 60 immediately adjacent the broadest spatial boundary of the primary irradiation zone 64 and the second ring 80 is disposed immediately adjacent the broadest spatial boundary of the secondary irradiation zone 76. A diameter of the first ring 78 and the second ring 80 increase proportionally with the vertical distance between the lamp 26 and the center portion 62 of the irradiation zone an equal amount to the broadest spatial boundary of the primary irradiation zone 64 and the secondary irradiation zone 76. In this manner, the identifier light source lens 82 is configured in a correlated manner so that angular displacement of the refracted light generates rings 78, 80 that increase in diameter at a same rate as does the UVC light in each of the first irradiation zone 64 and the second irradiation zone 76. Furthermore, the rings 78, 80 are transmitted on three dimensional surfaces providing identification that an object on a flat surface is within the irradiation zones 64, 76. The combination of the rings 64, 76 and the distance measuring device 56 providing user feedback via the indicator 24 enables a user, for example, to ascertain the viability of pathogen eradication that is achieved when used on inanimate objects and even on hands or other parts of the human anatomy.

The invention has been described is in an illustrative manner; many modifications and variations of the present invention are possible, including removal of toxins from fluids, in light of the above teachings. It is therefore to be understood that within the specification, the reference numerals are merely for convenience, and are not to be in any way limiting, and that the invention may be practiced otherwise than is specifically described. Therefore, the invention can be practiced otherwise than is specifically described within the scope of the stated claims following this first disclosed embodiment.

What is claimed is:

1. A handheld light assembly for irradiating pathogens on a surface, comprising:
   a housing;
   a lamp disposed in said housing for irradiating surfaces with disinfecting ultraviolet light having a single peak wavelength of about 222 nm thereby generating an irradiation zone on the surface;
   a processor programmed with a predetermined distance between the surface and said lamp for optimal transmission of irradiance to said surface from said lamp;
   a distance measuring device being offset from said lamp and including a transmitter for transmitting an invisible distances signal from said offset position toward the surface being irradiated and a sensor for receiving the transmitted signal reflected from the surface;
   said transmitter being oriented to transmit the distance signal from the offset position to a central portion of the irradiation zone on the surface being irradiated for identifying distance between said lamp and said surface being irradiated; and
   said processor programmed to calculate distance between said lamp and the central portion of the irradiation zone at the surface being irradiated from said signal transmitted from said offset position for providing user feedback that said lamp is disposed at the predetermined distance from surface at the central portion of the irradiation zone.

2. The assembly set forth in claim 1, wherein said distance measuring device is oriented for transmitting said signal to a measurement area that intersects the irradiation zone.

3. The assembly set forth in claim 1, wherein said distance measuring device is oriented for transmitting said signal to a measurement area that intersects the central portion of the irradiation zone.

4. The assembly set forth in claim 1, wherein said processor is programmed to determine distance being normal from said lamp to the surface from a signal transmitted by said transmitter at an offset angle to said lamp.

5. The assembly set forth in claim 1, further including a band pass filter disposed between said lamp and the surface being irradiated thereby filtering ultraviolet light above 230 nm.

6. The assembly set forth in claim 1, wherein said distance measuring device comprise a lidar system.

7. The assembly set forth in claim 1, wherein said distance measuring device comprise at least one of infrared, radar, and photogrammetry systems.

8. The assembly set forth in claim 1, further including an identifier light source for projecting visible light onto the surface being irradiated thereby identifying a primary and a secondary irradiation zone.

9. The assembly set forth in claim 1, further including an indicator being electronically connected to said processor for signaling optimal distance between the surface and said lamp is being maintained.

10. The assembly set forth in claim 1, wherein said lamp is disposed for transfer at least 3030 W of ultraviolet energy when a distance of one inch is disposed between said lamp and the surface being irradiated.

11. The assembly set forth in claim 1, wherein said lamp is disposed for transfer at least 1650 µW of ultraviolet energy when a distance of two inches is disposed between said lamp and the surface being irradiated.

12. The assembly set forth in claim 1, wherein said lamp is disposed for transfer at least 634 µW of ultraviolet energy when a distance of four inches is disposed between said lamp and the surface being irradiated.

13. The assembly set forth in claim 1, wherein said lamp is disposed for transfer at least 353 µW of ultraviolet energy when a distance of six inches is disposed between said lamp and the surface being irradiated.

14. The assembly set forth in claim 1, wherein a fused silica lens is disposed between said lamp and the surface being irradiated providing an inversely proportional reduction of ultraviolet energy relative to distance from the surface being irradiated.

15. The assembly set forth in claim 1, wherein said lamp transmits ultraviolet light in a range between 200 nm and 230 nm.

16. The assembly set forth in claim 1, further including a band pass filter for filtering ultraviolet light transmitted by said lamp above 230 nm.

* * * * *